May 22, 1956 YOSHIMATSU NISHIZAWA Plant Pat. 1,479
DIOSMA PLANT
Filed Nov. 20, 1950
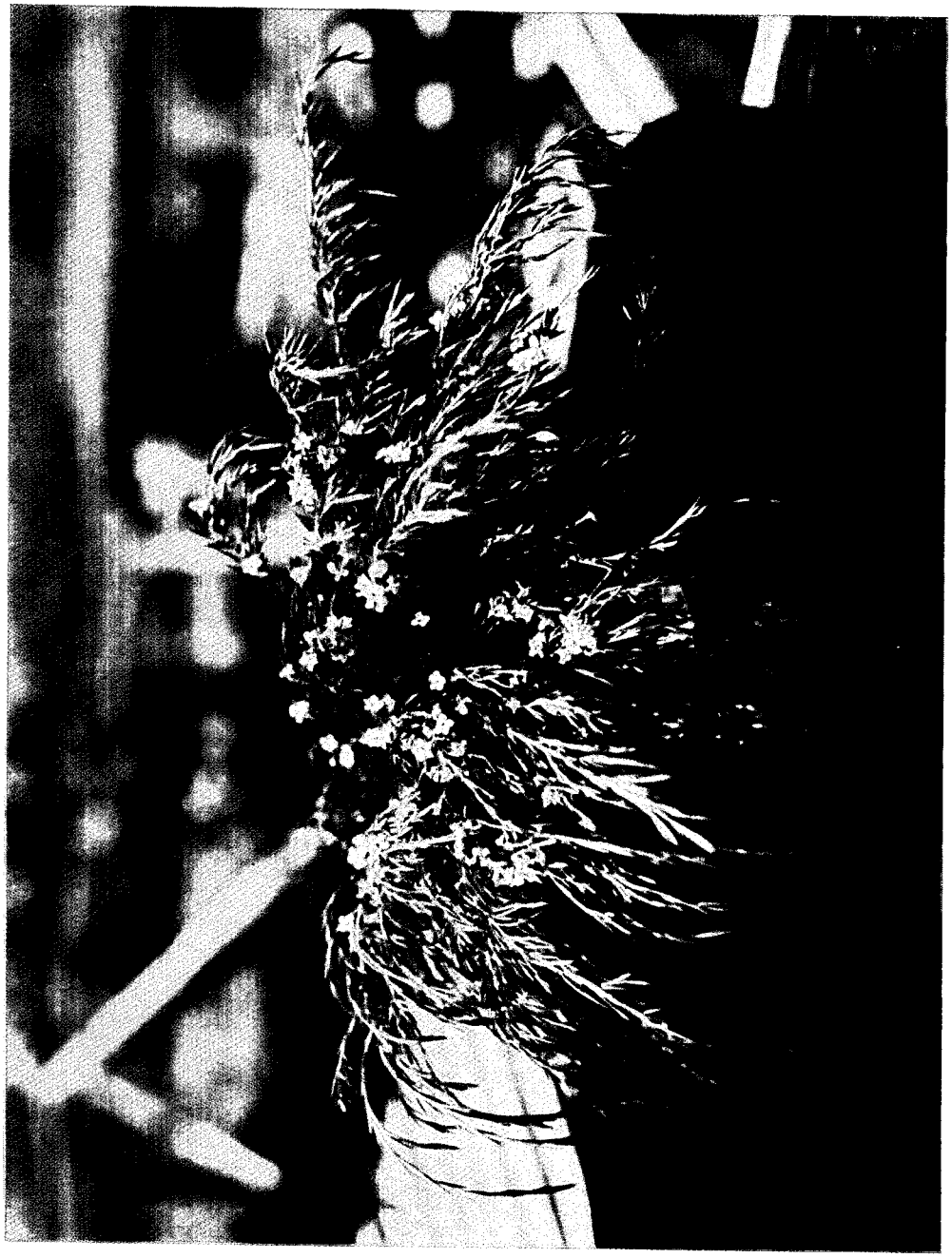
INVENTOR
YOSHIMATSU NISHIZAWA
BY Lyon & Lyon
ATTORNEYS United States Patent Office Plant Pat. 1,479
Patented May 22, 1956

1,479

DIOSMA PLANT

Yoshimatsu Nishizawa, West Los Angeles, Calif.

Application November 20, 1950, Serial No. 196,547

1 Claim. (Cl. 47—60)

This invention relates to a new and distinctive variety of Diosma which has as its parentage *Coleonema album* Bartling and Wendl (unpatented) crossed with the *Coleonema pulchrum* Hook (unpatented).

The Diosma was produced through cross-pollenization of these Diosma varieties, the cross-pollenization having been carried out at West Los Angeles, California. This variety of plant has been asexually reproduced by cuttings at 2238 Sawtelle Boulevard, Los Angeles, California.

The new and distinctive variety of Diosma embracing this invention is characterized by the following:

1. The plant is a compact rounded bush with somewhat pendulous branches approximately doubling in size annually and a one-year old plant is approximately one foot high having a fifteen inch spread.

2. The foliage has alternating leaves, linear about seven to fifteen millimeters long and one millimeter wide. The leaves are longer than the internodes, ascending to spreading and have a color shading from pea-green of chart 61/2 to 61/3 of the color plates of the Royal Horticultural Society color chart issued by the British Colour Council.

3. The bloom is seven to ten millimeters broad, the claws of the petals forming a tube three to five millimeters long. The blades are obovate, about four millimeters long, three millimeters broad, acute, rotate-salverform and membranous. The peak of bloom is from January to April with the fullest bloom in February and March. The color of the flower is white when the bud opens and changing until upon maturity it is a variegated color between white and carmine rose of charts 21/1, 21/2 and 21/3 of the color plates of the aforestated Royal Horticultural Society. The bud is four to five millimeters long and conical and is pink and white.

4. The seed production is similar to that of the parents and fertile pollen is abundantly produced.

5. The whole plant has a spicy odor.

6. The stem has a color shading from garnet brown 00918 to 00918/1 of the color plates of the aforestated Royal Horticultural Society.

7. The stamens have a color shading from white to pea green 61/3 of the color plates of said Royal Horticultural Society and the anther has a color similar to 00918/3 of said Royal Horticultural Society.

I claim:

A new and distinctive variety of Diosma plant characterized as to novelty by the compactness of the bush and the habit of producing profuse blossoms in greater quantity than can be found on its parents, said blossoms developing into a variegated coloring shaded between white and carmine-rose, substantially as described and illustrated.

No references cited.